US009109997B2

(12) United States Patent
Urban

(10) Patent No.: US 9,109,997 B2
(45) Date of Patent: Aug. 18, 2015

(54) METHOD FOR DETERMINING AND/OR MONITORING AT LEAST ONE PHYSICAL, PROCESS VARIABLE OF A MEDIUM

(75) Inventor: Martin Urban, Lorrach (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 511 days.

(21) Appl. No.: 13/387,172

(22) PCT Filed: Jun. 22, 2010

(86) PCT No.: PCT/EP2010/058801

§ 371 (c)(1), (2), (4) Date: Jan. 26, 2012

(87) PCT Pub. No.: WO2011/012377

PCT Pub. Date: Feb. 3, 2011

(65) Prior Publication Data

US 2012/0119758 A1 May 17, 2012

(30) Foreign Application Priority Data

Jul. 27, 2009 (DE) .......................... 10 2009 028 022

(51) Int. Cl.
*G01R 27/28* (2006.01)
*G01N 29/036* (2006.01)
(Continued)

(52) U.S. Cl.
CPC .......... *G01N 29/036* (2013.01); *G01F 23/2965* (2013.01); *G01F 23/2967* (2013.01);
(Continued)

(58) Field of Classification Search
CPC ..... G01N 29/075; G01F 23/2967; G01F 1/00; G01R 27/28
USPC ......... 324/617; 310/317; 702/159; 73/64, 53, 73/290 V See application file for complete search history.

(56) References Cited

U.S. PATENT DOCUMENTS 5,237,288 A * 8/1993 Cleveland ...................... 330/107
5,844,491 A * 12/1998 Getman et al. ................. 340/612
(Continued)

FOREIGN PATENT DOCUMENTS

DE 202007017911 U1 4/2008
DE 102007008669 A1 8/2008
(Continued)

OTHER PUBLICATIONS

English translation of IPR.
(Continued)

*Primary Examiner* — Arleen M Vazquez
*Assistant Examiner* — Brent J Andrews
(74) *Attorney, Agent, or Firm* — Bacon & Thomas, PLLC

(57) ABSTRACT

A method for determining and/or monitoring at least one physical, process variable of a medium with an oscillatable unit, wherein the oscillatable unit is excited by means of a frequency search sweep within a predetermined frequency band in the working range of the oscillatable unit in the form of transmitted signals successively to oscillate with discrete exciter frequencies wherein the corresponding oscillations of the oscillatable unit are received in the form of received signals, wherein, via the frequency search sweep, the exciter frequency is ascertained, in the case of which the oscillatable unit oscillates with an oscillation frequency, which has a predetermined phase shift between the transmitted signal and the received signal. The transmitting/receiving unit excites the oscillatable unit to oscillate with the ascertained oscillation frequency. The selected points in time depend on the predetermined phase shift between transmitted signal and received signal and that the voltage values sampled at the discrete exciter frequencies of the received signal are evaluated with reference to their amplitude.

13 Claims, 4 Drawing Sheets

(51) Int. Cl.
*G01F 23/296* (2006.01)
*G01N 9/00* (2006.01)
*G01N 11/16* (2006.01)
*G01N 29/02* (2006.01)

(52) U.S. Cl.
CPC ........ *G01N9/002* (2013.01); *G01N 11/16* (2013.01); *G01N 29/022* (2013.01); *G01N 2291/02818* (2013.01); *G01N 2291/02836* (2013.01); *G01N 2291/0427* (2013.01)

(56) References Cited

U.S. PATENT DOCUMENTS

| | | | |
|---|---|---|---|
| 6,906,450 B2 * | 6/2005 | Tamayo De Miguel et al. | 310/317 |
| 2006/0131994 A1 * | 6/2006 | D'Angelico et al. | 310/317 |
| 2006/0142954 A1 * | 6/2006 | Muller et al. | 702/30 |
| 2007/0100578 A1 * | 5/2007 | Wrobel | 702/159 |
| 2009/0205411 A1 | 8/2009 | Muller | |
| 2010/0161251 A1 | 6/2010 | D'Angelico | |
| 2012/0085165 A1 * | 4/2012 | Hortenbach et al. | 73/290 V |

FOREIGN PATENT DOCUMENTS

| | | |
|---|---|---|
| DE | 102005015547 A1 | 10/2009 |
| EP | 0985916 A1 | 3/2000 |
| WO | WO 2009/083050 A1 | 7/2009 |

OTHER PUBLICATIONS

International Search Report.

* cited by examiner

METHOD FOR DETERMINING AND/OR MONITORING AT LEAST ONE PHYSICAL, PROCESS VARIABLE OF A MEDIUM

TECHNICAL FIELD

The present invention relates to a method for determining and/or monitoring at least one physical, process variable of a medium with an oscillatable unit, wherein the oscillatable unit is excited by means of a frequency search sweep within a predetermined frequency band in the working range of the oscillatable unit in the form of transmitted signals successively to oscillate with discrete exciter frequencies following one after the other The corresponding oscillations of the oscillatable unit are received in the form of received signals, wherein, via the frequency search sweep, that exciter frequency is ascertained, in the case of which the oscillatable unit oscillates with an oscillation frequency, which has a predetermined phase shift between the transmitted signal and the received signal, wherein a transmitting/receiving unit excites the oscillatable unit to oscillate with the ascertained oscillation frequency or wherein the following frequency search sweep is started. The process variable is, for example, a predetermined fill level of the medium, the phase boundary, the density or the viscosity of the medium.

BACKGROUND DISCUSSION

With vibronic measuring devices, a large number of physical variables can be detected or monitored, such as, for example, the fill level, the phase boundary, the density or the viscosity of a medium in a container or in a pipeline. The Endress+Hauser Group provides such measuring devices in a large variety under the marks, LIQUIPHANT and SOLIPHANT.

Vibronic measuring devices have an oscillatable unit, which, most often, includes a membrane and an oscillatory rod secured thereon or an oscillatory fork having two tines. There are, however, also vibronic measuring devices known, whose osciiatable unit is only the membrane.

The exciting of the oscillatable unit to oscillate with the resonance frequency occurs usually via a piezoelectric stack- or bimorph drive or via electrodynamic drive elements, wherein the drive unit, most often, is embodied as a combined transmitting/receiving unit. The transmitted signal and the received signal have a phase shift, which usually lies in a defined range around 90°.

For fill level measurement, the effect is utilized that the oscillation frequency and oscillation amplitude change, when the degree of covering of the oscillatable unit changes. In air, undamped oscillation occurs, while oscillation is damped in the case of an oscillatable unit covered with medium. This change in the oscillation amplitude or oscillation frequency is utilized to detect the reaching of a predetermined fill level, usually a maximum fill level, for overflow protection or a minimum fill level for protection against running empty.

The oscillation amplitude of an oscillatory fork or of an oscillatory rod depends furthermore on how much mass is being dragged. If the density or the phase of a medium changes, then this influences the oscillation of the oscillatable unit, so that a transition between different phases as well as also density changes can be detected with the vibronic measuring device. In a similar manner, the oscillation is damped when the viscosity of the medium increases.

In order to so set the exciter frequency that the oscillatable unit oscillates with a predetermined phase shift between transmitted signal and received signal, the Endress+Hauser Group has developed a method utilizing a frequency search sweep. A corresponding German patent application (Application No. DE 102009026685) has been filed but has not yet been published. The method will be described briefly here.

In the frequency search sweep, the oscillatable unit is excited successively to oscillate with discrete, closely neighboring frequencies and the frequency corresponding to the predetermined phase shift is ascertained. The ascertaining of the frequency occurs, in such case, via phase selective rectification and following low-pass filtering. A rectangular signal delayed by the predetermined phase shift relative to a received signal is multiplied with the received signal. If the phase shift between the transmitted signal and the received signal corresponds to the predetermined phase shift, then this product contains only positive portions, while in the opposite case, it would contain negative portions. The described evaluation methods can be implemented analogly or digitally. The embodiment with analog components has, in such case, two disadvantages. On the one hand, the circuit complexity is high and, on the other hand, the determining of the oscillation frequency at the predetermined phase shift is relatively inaccurate. The advantages in the case of the digital practice of the method include that the high circuit complexity is absent and, additionally, the oscillation frequency can be determined with high accuracy. The disadvantage of the digital method is, however that it is very calculation intensive, which makes a high computing power necessary.

SUMMARY OF THE INVENTION

An object of the invention, consequently, is to provide a method for the simple evaluation of a frequency search sweep.

The object is achieved by the features including that the oscillation frequency at the predetermined phase shift is ascertained by sampling the received signal discretely at selected points in time, wherein the selected time points depend on the predetermined phase shift between the transmitted signal and the received signal, and that the voltage values Ui of the received signal sampled at the discrete exciter frequencies are evaluated with reference to amplitude.

Since the received signal is sampled discretely only at selected points in time, the number of measurement points, which are stored and further processed, is reduced compared to methods, in the case of which the entire received signal is further processed. In this way, the computing power required is reduced. A further advantage is that the evaluation occurs essentially digitally, which saves time and manufacturing costs compared with analog practice. The used components can have high tolerances, since, for example, noise is filtered out, so that exact results are achieved nevertheless.

In a first embodiment of the solution of the invention, for evaluating sampled voltage values $U_i$ of the received signal, negative portions of the received signal are converted, by rectification or by adding an offset voltage, into positive voltage values. The received signal is an alternating voltage. Before digitizing for evaluating the received signal the therein contained, negative portions are preferably converted into positive portions, in order to make the received signal useful for an analog-digital converter, which can only process positive input voltages. If an analog-digital converter is used, which can process both negative as well as also positive input voltages, then the changing into positive signals is not required. The changing into positive voltage values is accomplished either by rectification, i.e. through inverting the negative voltage values, or by adding a direct voltage to the alternating voltage, so that the entire voltage curve is shifted by a certain value (offset) into the positive region. The offset is selected, in such case, in order, on the one hand, that all negative voltage values are shifted into the positive region, and, on the other hand, the value of the maximum arising voltage does not exceed the allowable maximum input voltage of the analog-digital converter.

In a further development of the method of the invention, the received signal is always sampled at points in time, when it, in the case of the presence of the predetermined phase shift between the transmitted signal and the received signal, passes through an extreme. Thus, per oscillation period, always two voltage values of the received signal are sampled.

In the case of an additional further development of the invention, for the case, in which the predetermined phase shift amounts to 90°, the received signal is always sampled at points in time, when the transmitted signal, in the case of the presence of the predetermined phase shift, passes through zero.

A further development of the method of the invention provides that the sampled voltage values $U_i$ of the received signal are evaluated by determining the frequency, at which the magnitude $|U_i|$ of the voltage value is maximum. If the received signal at a frequency $f_k$ corresponds to an oscillation with the predetermined phase shift, then the voltage value detected at the sampling points in time corresponds to the maximum oscillation amplitude. If the received signal at a frequency $f_l$ does not correspond to the oscillation with the predetermined phase shift, then the maximum amplitude is not detected at the sampling points in time, but, instead a lesser voltage value. If one plots the voltage values at different frequencies determined at the sampling points in time, then there results a curve with a maximum at the frequency $f_k$, where the transmitted signal and the received signal have the predetermined phase shift.

A further development of the method of the invention provides that the sampled voltage values $U_i$ of the received signal are evaluated by adding the magnitudes of the voltage values MI sampled over a number of oscillation periods of equal frequency to a value $\Sigma|U_i|$, and the frequency is determined, at which the associated value $\Sigma|U_i|$ is maximum.

A further development of the solution of the invention provides that the received signal is sampled always at points in time, at which, in the presence of the predetermined phase shift between the transmitted signal and the received signal, it passes through zeros and extrema. Per oscillation period, there are thus four voltage values sampled.

In the case of a further development of the method of the invention, for the case, in which the predetermined phase shift amounts to 90°, the received signal is always sampled at points in time when the transmitted signal, in the case of the presence of the predetermined phase shift, passes through zero and at points in time, at which the transmitted signal, in the case of the presence of the predetermined phase shift, passes through an extreme.

In a further development of the method of the invention, the sampled voltage values $U_{ii}$, $U_{ij}$ of the received signal are evaluated by subtracting from one another the magnitudes, in each case, of two sequential voltage values $|U_{ii}|$, $|U_{ij}|$, which correspond, at the predetermined phase shift, to the voltage value at a zero traverse and the magnitude of the voltage value at an extreme of the received signal, and the frequency is determined to be that at which the difference $\Delta U = |U_{ii}| - |U_{ij}|$ has maximum magnitude. If the measured voltage values $|U_{ii}|$ of the maximum voltage values, which occur at the respective frequency, by a magnitude $dU_{ii}$ and the measured voltage values $|U_{ij}|$ differ from zero by a magnitude $dU_{ij}$, then the difference $\Delta U$ differs by $dU_{ii} + dU_{ij}$ from the maximum voltage value at the respective frequency. If one considers only the voltage values, which, in the case of predetermined phase shift, correspond to extrema, then these differ by a smaller value, namely $dU_{ii}$, from the maximum voltage value, which occurs at the respective frequency. If the predetermined phase shift is present, then there results in the case of the difference forming between the value, in the case of the maximum and the value, in the case of the zero traverse, the same (maximum) voltage value, which results only through consideration of the maximum. Therefore, is the maximum around the frequency corresponding to the desired phase shift in the case of consideration of the differences $\Delta U$ more marked than in the case of the method, in the case of which only the voltage values are sampled and evaluated, which, at predetermined phase relationship, correspond to the maximum,.

In a further development of the solution of the invention, the voltage values $U_{ii}$, $U_{ij}$ of the received signal sampled over a number of oscillation periods of equal frequency are so evaluated that the magnitudes of the sampled voltage values $|U_{ii}|$, which were sampled at points in time, which, at the predetermined phase shift, correspond to the position of an extreme, are added to a value $U_{max}$, that the magnitudes of the sampled voltage values $|U_{ij}|$, which were sampled at points in time, which, at the predetermined phase shift, correspond to the position of a zero traverse, are added to a value $U_{zero}$, that the values $U_{max}$ and $U_{zero}$ are subtracted from one another and that the frequency is determined, at which the difference $\Delta U = U_{max} - U_{zero}$ has maximum magnitude. For each frequency, thus, in each case, only one voltage value is taken into consideration for determining the frequency at the predetermined phase shift.

A further development of the method of the invention provides that a phase shift between the transmitted signal and the received signal is set, which depends on the quality of the oscillatable unit.

In an additional further development of the solution of the invention, a phase shift between the transmitted signal and the received signal is set, which lies preferably in the range between 70° and 120°. The predetermined phase shift amounts, most often, to 90° or lies preferably in the stated range. It is, however, equally possible that it assumes a value outside of the stated range, to the extent that the quality of the oscillatable unit permits this.

Another further development of the invention provides that the physical measured variable is a predetermined fill level of the medium, the density, the viscosity, or the phase boundary of the medium. If a predetermined fill level of the medium in a container is to be detected, then the oscillatable unit is placed at the height of the predetermined fill level.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1A:
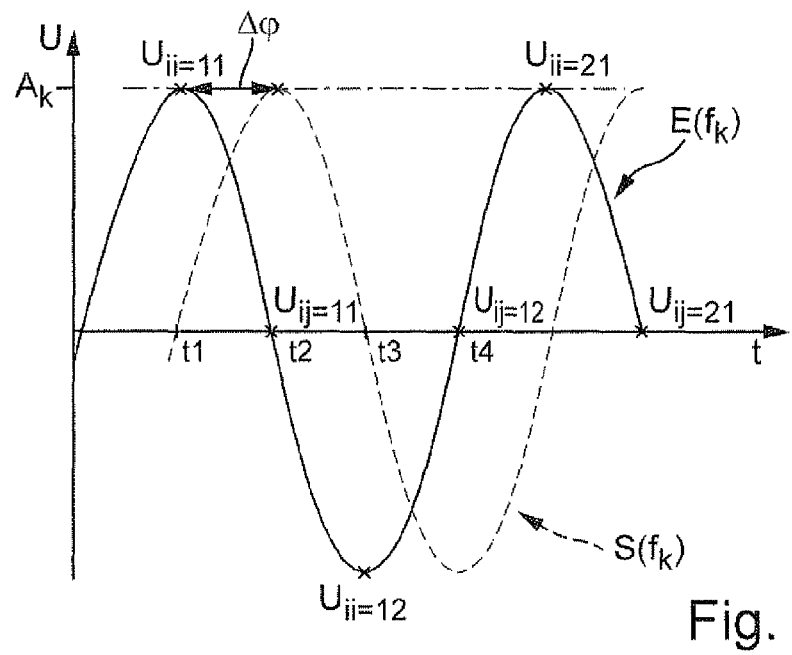
FIG. 1a is an example of the positioning of the sampling points in the case of a received signal with the frequency fk corresponding to the predetermined phase shift.

FIG. 1a shows the received signal R at an exciter frequency fk over one and one half periods. For comparison, the transmitted signal T is likewise plotted. In FIG. 1a, the exciter frequency fk corresponds to the predetermined phase shift $\Delta\phi$ between the transmitted signal T and the received signal R. At the sampling points in time, the received signal R is located in zero traverses or extrema, The sampled voltage values Uii correspond, consequently, to the maximum arising voltage value Ak, thus the amplitude, at this exciter frequency fk and the sampled voltage values Uij are zero. In this example, only the sampling points in time lying within a period are presented. Of course, samples at an exciter frequency fk over a number of periods can occur, in order to achieve better statistics.

For the case shown here, in which the predetermined phase shift $\Delta\phi$ between transmitted signal T and received signal R amounts to 90°, the zero traverses of the transmitted signal T coincide with the extrema of the received signal R and the extrema of the transmitted signal T with the zero traverses of the received signal R. Relative to the transmitted signal T, the received signal R is thus always sampled at points in time, when the transmitted signal T passes through a zero or an extreme.

Figure 1B:
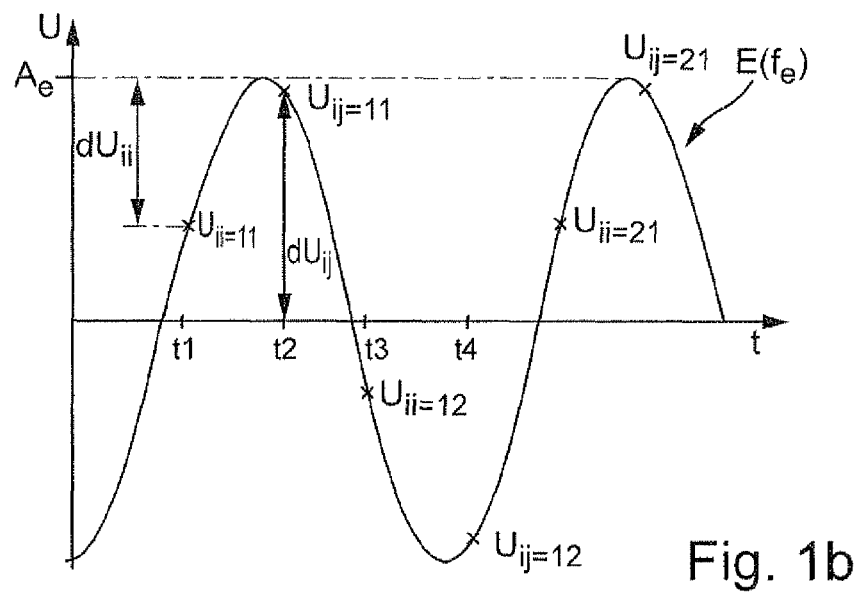
FIG. 1b is an example of the positioning of the sampling points in the case of a received signal with the frequency fl lying outside the predetermined phase shift.

FIG. 1b shows a received signal R with an exciter frequency which is located outside the predetermined phase shift $\Delta\phi$ for the transmitted signal T. The sampling points in time, consequently, do not coincide with the points in time, at which the received signal R passes through a zero or an extreme. The sampled voltage values $U_{ii}$ differ from the maximum voltage value $A_l$ by a value $dU_{ii}$ and the sampled voltage values $U_{ij}$ differ from zero by a value $dU_{ij}$.

Figure 1C:
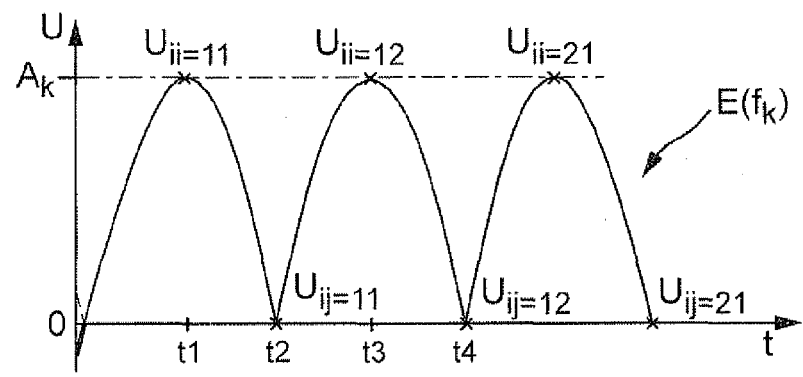
FIG. 1c shows the received signal of FIG. 1a after rectification.
Figure 1D:
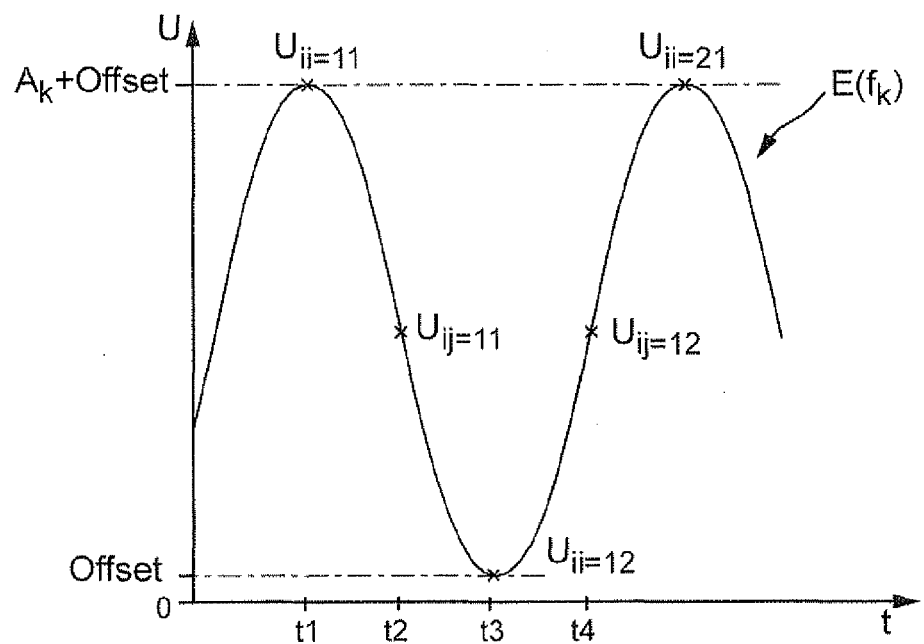
FIG. 1d shows the received signal of FIG. 1a after adding a direct voltage.

The received signals R illustrated in FIGS. 1a and 1b are alternating voltages and the voltage values $U_{ii}$, $U_{ij}$ at the sampling points in time are partially negative. In a preferred embodiment of the method, the received signal R is so modified before the sampling that only positive voltage values remain. This is accomplished, for example, by inverting, or rectifying, the negative voltage portions. FIG. 1c shows the received signal R of FIG. 1a after rectification. Another opportunity for changing the negative voltage portions is to add a direct voltage to the received signal R. In this way, the entire voltage curve forming the received signal is shifted by a certain value, the so-called offset, into the positive region. The received signal R modified in this way is shown in FIG. 1d. Since this offset is the same for all exciter frequencies $f_k$ contained in the frequency search sweep, all sampled voltage values $U_{ii}$, $U_{ij}$ are shifted by the same value. If an offset is added to the received signal, then this value must be taken into consideration in the evaluation of the sampled voltage values $U_{ii}$, $U_{ij}$, since, for example, the voltage value $U_{ij}$ in the case of a zero and presence of the predetermined phase shift $\Delta\phi$ is not zero, but, instead, corresponds to the value of the offset voltage.

Figure 2:
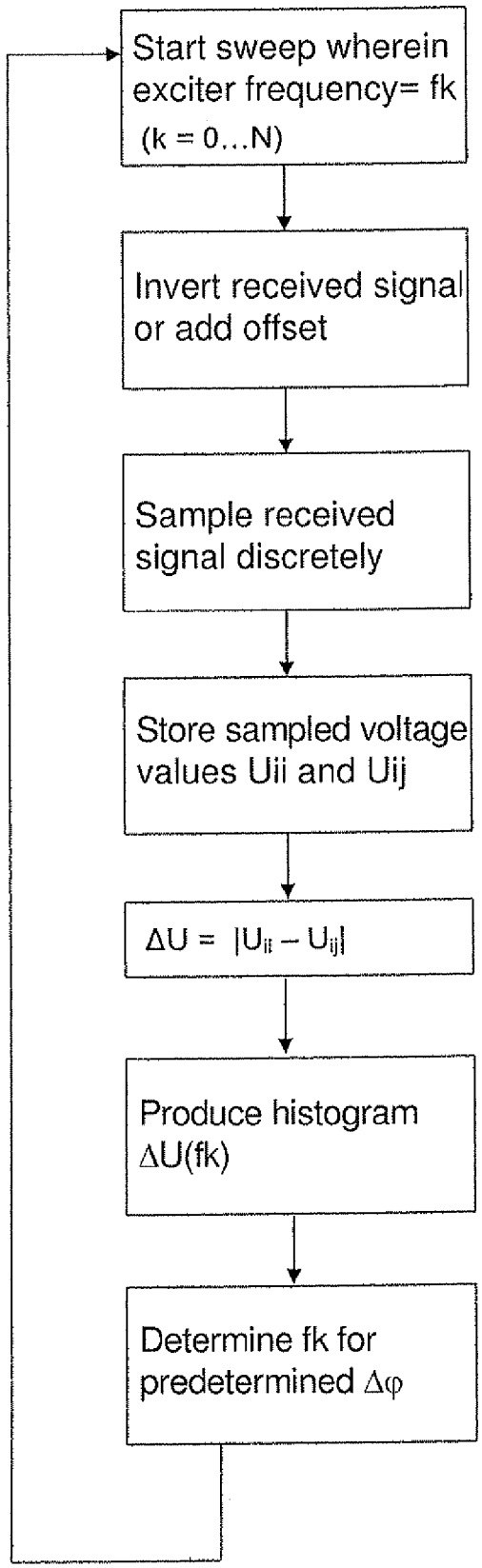
FIG. 2 is a flow diagram of the method of the invention.

FIG. 2 discloses a flow diagram of an example of an embodiment of the method of the invention. In the following, it is assumed that the received signal R contains only positive portions because of rectifying or addition of a direct voltage. Application of a sign was therefore omitted. It should, however, be noted that in the case, in which no such modification of the received signal R has taken place, the magnitudes, or absolute values, of negative voltage values are formed.

During the frequency search sweep, the oscillatable unit is excited with discrete exciter frequencies $f_k$ (k=0 ... N) within the total working range. The goal is to filter out that exciter frequency $f_k$, in the case of which the transmitted signal T and the received signal R have a predetermined phase shift $\Delta\phi$, for example, 90°. For this, a transmission signal T with a first exciter frequency $f_0$ is produced. The received signal R is sampled at selected points in time. The points in time are, in such case, then selected such that, in the case of predetermined phase shift $\Delta\phi$, the extrema and the zero traverses of the received signal R are detected. In the case of a predetermined phase shift $\Delta\phi=90°$, these are the points in time, at which the transmitted signal T traverses zero and extrema.

The voltage values $U_{ii}$ sampled at expected extrema and voltage values $U_{ij}$ sampled at expected zero traverses are stored. The sampled and stored voltage values $U_{ii}$, $U_{ij}$ are processed, by subtracting, in each case, a voltage value $U_{ii}$, which corresponds to an expected extreme, from a thereon following voltage value $U_{ij}$, which corresponds to an expected zero-point,. After an established number of oscillation periods, the next exciter frequency $f_k$ is set.

If the exciter frequency $f_k$ is that, in the case of which the phase shift $\Delta\phi$ corresponds to the predetermined phase shift $\Delta\phi$, then the voltage values $U_{ii}$ sampled at expected extrema correspond to the maximum voltage value, which occurs for the particular exciter frequency $f_k$, thus the amplitude $A_k$ of the oscillation. The voltage values $U_{ij}$ sampled at expected zero traverses are zero. If, however, the exciter frequency $f_k$ differs from the exciter frequency $f_k$, in the case of which the predetermined phase shift $\Delta\phi$ is present, then the voltage values $U_{ii}$, $U_{ij}$ detected at the sampling points in time are smaller than the associated amplitude $A_k$ or greater than zero. The voltage value $U_{ii}$, which is detected, is thus not the maximum voltage value $A_k$, which occurs in the case of the respective exciter frequency $f_k$. If one forms the difference, in each case, of the two voltage values $U_{ii}$ and $U_{ij}$, which were sampled in the case of the expected zero traverse and in the case of the expected extreme, then this difference $\Delta U$ is smaller than the difference $\Delta U$ at the predetermined phase shift $\Delta\phi$. At the predetermined phase shift $\Delta\phi$, the difference $\Delta U$ equals the amplitude $A_k$ of the received signal and, thus, is maximum. If to the received signal an offset is added, in order to obtain purely positive voltage values, then this value must be appropriately taken into consideration in the case of evaluating the sampled voltage values $U_{ii}$, $U_{ij}$.

An alternative embodiment of processing the voltage values $U_{ii}$, $U_{ij}$ sampled at an exciter frequency $f_k$ provides that all voltage values $U_{ii}$ sampled in the case of an expected extreme are added to a value $U_{max}$, that all voltage values $U_{ij}$ sampled in the case of an expected zero traverse are added to a value $U_{zero}$, and that then the difference $\Delta U=|U_{max}-U_{zero}|$ is formed.

In this way, one obtains an averaged voltage value for each exciter frequency $f_k$.

In an additional method step, the formed voltage differences $\Delta U$ are plotted versus the respective exciter frequencies $f_k$. The resulting histogram has a maximum at the exciter frequency $f_k$ corresponding to the predetermined phase shift $\Delta\phi$.

In this example of an embodiment, both expected zero traverses as well as also expected extrema are sampled and then the difference $\Delta U$ between the voltage values $U_{ii}$, $U_{ij}$ is formed. In an alternative embodiment of the method, the received signal R is sampled only at points in time of expected extrema. If the received signal R in the case of the exciter frequency $f_k$ corresponds to an oscillation with the predetermined phase shift $\Delta\phi$, then the oscillation amplitude $A_k$ is detected. If the received signal R in the case of the exciter frequency $f_k$ does not correspond to the oscillation with the predetermined phase shift $\Delta\phi$, then not the amplitude $A_k$ is detected, but, instead, a lesser value. If one plots the voltage values $U_{ii}$ determined at different exciter frequencies $f_k$, then there results a curve with a maximum at that exciter frequency $f_k$, in the case of which the transmitted signal T and the received signal R have the predetermined phase shift Δϕ. Analogously to the case described for the difference forming, the sampled voltage values $U_{ii}$ over a number of oscillation periods can be added up, so that in the histogram per exciter frequency $f_k$ only a voltage value $\Sigma U_{ii}$ is stated. Alternatively, an option is to list all sampled voltage values $U_{ii}$ separately.

It is provided that as soon as a frequency search sweep is ended, a renewed frequency search sweep is started, the frequency search sweeps thus are performed continuously. In this way, changed process conditions can be rapidly reacted to and the oscillation frequency of the oscillatable unit can be immediately adjusted. Alternatively, for this, the oscillatable unit is excited with the exciter frequency $f_k$ determined in the frequency search sweep. Renewed frequency search sweeps occur then, for example, instead, at determined intervals or are started on request.

Figure 3:
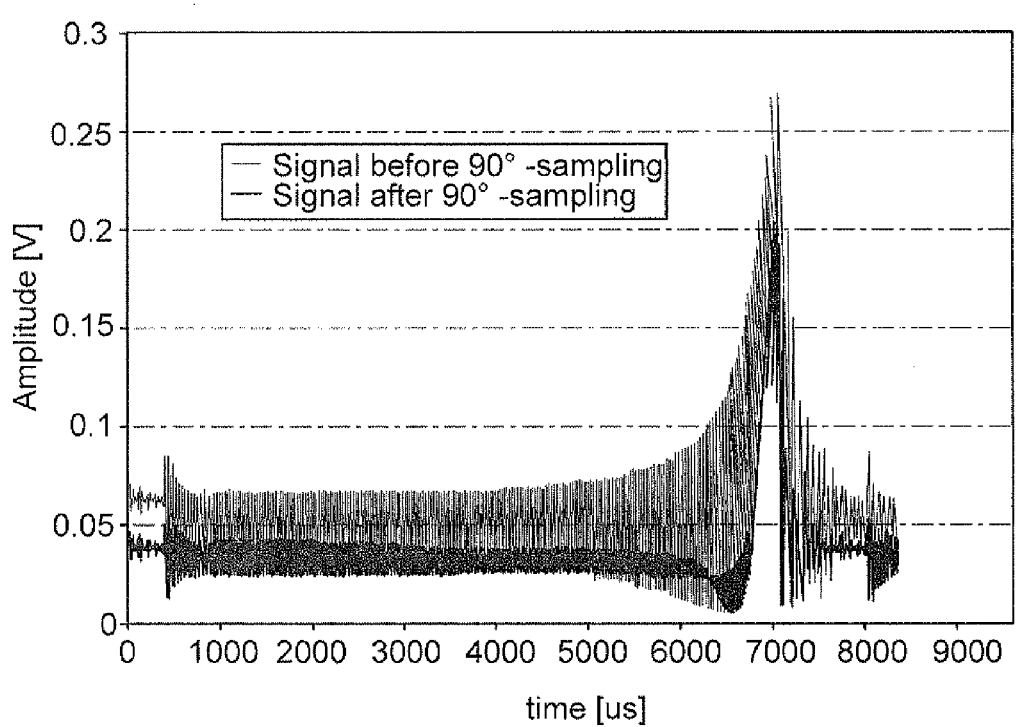
FIG. 3 is the histogram recorded for determining the frequency at the predetermined phase shift.

FIG. 3 shows a histogram for determining that exciter frequency $f_k$, in the case of which the transmitted signal T and the received signal R have the predetermined phase shift Δϕ. Besides the received signal R sampled according to the method described in FIG. 2, also shown is the received signal R before the sampling. The maximum at the exciter frequency $f_k$ corresponding to the predetermined phase shift Δϕ is clearly evident in both curves. The sampled received signal R is, however, more sharply defined and has a higher ratio of maximum to baseline. The received signal R shown in this histogram is for a membrane oscillator.

The invention claimed is:

1. A method for determining and/or monitoring at least one physical, process variable of a medium with an oscillatable unit, comprising the steps of:
exciting the oscillatable unit by means of a frequency search sweep within a predetermined frequency band in the working range of the oscillatable unit in the form of transmitted signals successively to oscillate with discrete exciter frequencies following one after the other;
receiving corresponding oscillations of the oscillatable unit in the form of received signals,
ascertaining the exciter frequency via the frequency search sweep in the case of which the oscillatable unit oscillates with an oscillation frequency, which has a predetermined phase shift between the transmitted signal and the received signal;
a transmitting/receiving unit excites the oscillatable unit to oscillate with the ascertained oscillation frequency or the following frequency search sweep is started; and
ascertaining the oscillation frequency at a predetermined phase shift by sampling the received signal discretely at selected points in time, wherein:
the selected points in time depend on the predetermined phase shift between transmitted signal and received signal, and the voltage values of the received signal sampled at the discrete exciter frequencies are evaluated with reference to their amplitude.

2. The method as claimed in claim 1, further comprising the step of:
converting negative portions of the received signal, for evaluating sampled voltage values of the received signal by rectification or by adding an offset voltage, into positive voltage values.

3. The method as claimed in claim 1, wherein:
the received signal is always sampled at points in time, when it, in the case of the presence of the predetermined phase shift between transmitted signal and received signal, passes through an extreme.

4. The method as claimed in claim 1, wherein:
for the case, in which the predetermined phase shift amounts to 90°, the received signal is always sampled at points in time, when the transmitted signal, in the case of presence of the predetermined phase shift, passes through zero.

5. The method as claimed in claim 3, wherein:
the sampled voltage values of the received signal are evaluated by determining the exciter frequency at which the magnitude of the voltage value is maximum.

6. The method as claimed in claim 3, wherein:
the sampled voltage values of the received signal are evaluated by adding the magnitudes of the voltage values sampled over a number of oscillation periods of equal frequency to a value equal to the sum of the voltage values, and the exciter frequency is determined, at which the associated sum of the voltage value is maximum.

7. The method as claimed in claim 1, wherein:
the received signal is sampled always at points in time, at which, in presence of the predetermined phase shift between transmitted signal and received signal, it passes through zeros and extrema.

8. The method as claimed in claim 1, wherein:
for the case, in which the predetermined phase shift amounts to 90°, the received signal is always sampled at points in time when the transmitted signal, in the case of the presence of the predetermined phase shift, passes through zero and at points in time, at which the transmitted signal passes through an extreme.

9. The method as claimed in claim 7, wherein:
the sampled voltage values of the received signal are evaluated by subtracting from one another the magnitudes, in each case, of two sequential voltage values, which correspond, at the predetermined phase shift, to the magnitude of the voltage value at a zero traverse and the magnitude of the voltage value on an extreme of the received signal, and the exciter frequency is determined to be that at which the difference of the sequential voltage values has maximum magnitude.

10. The method as claimed in claim 7, wherein:
voltage values $U_{ii}$, $U_{ij}$ of the received signal sampled over a number of oscillation periods of equal frequency are so evaluated that the magnitudes of the sampled voltage values $|U_{ii}|$, which were sampled at points in time, which, at the predetermined phase shift, correspond to the position of an extreme, are added to a value $U_{max}$, the magnitudes of the sampled voltage values $|U_{ij}|$, which were sampled at points in time, which, at the predetermined phase shift, correspond to the position of a zero traverse, are added to a value $U_{zero}$, the values $U_{max}$ and $U_{zero}$ are subtracted from one another and the exciter frequency is determined, at which the difference $\Delta U = U_{max} - U_{zero}$ has a maximum magnitude.

11. The method as claimed in claim 1, wherein:
a phase shift between transmitted signal and received signal is set, which depends on the quality of the oscillatable unit.

12. The method as claimed in claim 1, wherein:
a phase shift between transmitted signal and received signal is set, which lies preferably in the range between 70° and 120°.

13. The method as claimed in claim 1, wherein:
the physical measured variable is a predetermined fill level of the medium in a container, density, viscosity, or a phase boundary of the medium.

* * * * *